United States Patent [19]

Itzerott

[11] 4,000,290

[45] * Dec. 28, 1976

[54] FUNGISTATIC COMPOSITION FOR TREATING SEEDS USING A MIXTURE OF A SUBSTITUTED BENZIMIDAZOLE AND 2-(THIOCYANOMETHYLTHIO)-BENZOTHIAZOLE

[75] Inventor: Heinz Itzerott, Grunstadt, Germany

[73] Assignee: C. F. Spiess & Sohn, Kleinkarlbach, Germany

[ * ] Notice: The portion of the term of this patent subsequent to Feb. 28, 1993, has been disclaimed.

[22] Filed: June 23, 1971

[21] Appl. No.: 156,054

[30] Foreign Application Priority Data

June 23, 1970 Germany .......................... 2030848

[52] U.S. Cl. .............................. 424/270; 424/273; 424/DIG. 8

[51] Int. Cl.² ..................... A01N 9/02; A01N 9/18; A01N 9/22

[58] Field of Search .............. 424/DIG. 8, 273, 270

[56] References Cited

FOREIGN PATENTS OR APPLICATIONS 1,129,575   10/1968   United Kingdom

OTHER PUBLICATIONS

Neumeyer et al., Chemical Week, p. 47, Apr. 12, 1969.

Primary Examiner—Albert T. Meyers
Assistant Examiner—Allen J. Robinson
Attorney, Agent, or Firm—Flynn & Frishauf

[57] ABSTRACT

A fungistatic composition containing as the active components (i) at least one of a group of specified substituted benzimidazoles exemplified by 1-(butylcarbamoyl)-2-benzimidazole carbamic acid methyl ester and (ii) 2-(thiocyanomethylthio)-benzothiazole in a weight ratio of said substituted benzimidazole to said benzothiazole of between 10:1 and 1:2, and preferably in a ratio between 5:1 and 2:1 with an optimum ratio of 3:1. The composition preferably contains an inert carrier. The invention also includes the process of treating seeds with said fungistatic composition.

3 Claims, No Drawings

FUNGISTATIC COMPOSITION FOR TREATING SEEDS USING A MIXTURE OF A SUBSTITUTED BENZIMIDAZOLE AND 2-(THIOCYANOMETHYLTHIO)-BENZOTHIAZOLE

FIELD OF INVENTION

This invention relates to the use of novel fungistatic compositions for treating seeds and particularly cereal seeds to effectively control fungus attack of said seeds.

BACKGROUND OF THE INVENTION

It is well known that fungal diseases caused by Helminthosporium species are particularly difficult to suppress by treating the seed of the cereal. The only successful treatment consists in using preparations containing organic mercury compounds as the active agent. However, since organic mercury compounds are toxic, it is desirable to replace them by non-toxic organic agents.

It has already been proposed to use 2-(thiocyanomethylthio)-benzothiazole in fungistatic compositions. It has also been proposed to use substituted benzimidazoles for the control of fungal diseases (French Patent Specification No. 105,412). This applies particularly to compounds of the formula

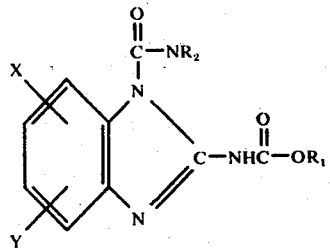

wherein X is selected from the group consisting of hydrogen, halogen, alkyl groups containing 1 to 4 carbon atoms, a nitro group and alkoxy groups containing 1 to 4 carbon atoms; Y is selected from the group consisting of hydrogen, chlorine and bromine; $R_1$ is selected from the group consisting of (i) alkyl groups containing 1 to 6 carbon atoms and such alkyl groups substituted with chlorine, bromine or a cyano group, (ii) alkenyl groups containing 3 to 6 carbon atoms, (iii) alkynyl groups containing 3 to 6 carbon atoms, (iv) benzyl, and (v) phenyl; and $R_2$ is selected from the group consisting of hydrogen, alkyl groups containing 1 to 6 carbon atoms, and alkenyl groups containing 2 to 6 carbon atoms. Compounds falling within the foregoing definition are referred to hereinafter as "said substituted benzimidazoles". In practice the 1-(butylcarbamoyl)-2-benzimidazole carbamic acid methyl ester has proven to be particularly useful. Each of these agents is known to exhibit fungicidal activity. However, they do not have sufficient efficacy for maximum control of the Helminthosporium species.

It is an object of the present invention to provide fungistatic compositions which are more effective than those which could be obtained using each of the aforesaid compounds.

SUMMARY OF THE INVENTION

It has now been found that a wide variety of fungi and particularly the Helminthosporium species can be controlled by application of a fungistatic composition containing as the active components (i) at least one of said substituted benzimidazoles and (ii) said 2-(thiocyanomethylthio)-benzothiazole in a weight ratio of between 10:1 and 1:2. The substrate, e.g. cereal seeds, to be protected from the fungus attack is physically contacted with the fungistatic composition to provide such protection.

SPECIFIC EMBODIMENTS OF THE INVENTION

It is a particular advantage that the fungistatic compositions of the present invention are effective not only in controlling the Helminthosporium species, but also very effective against other fungal diseases caused by all other fungi that attack cereal seeds such as Fisarium nivale — Wilts
Tilletia caries
Ustilago avenae — Oats smuts
Ustilago nudae — Loose smuts
Ustilago tritici — Wheat smuts
Septoria nodorum — Stem spot This means that a single treatment is sufficient for treating cereal seeds to suppress and control all fungal diseases that are likely to attack such seeds. Another advantage of the proposed combination is that it not merely attacks spores that adhere externally to the seed, but because of the good systemic activity of said substituted benzimidazoles also attacks the mycelium that penetrates the plant.

Contrary to organic mercury compounds the proposed mixture is practically non-toxic.

The preferred fungistatic compositions contain the substituted benzimidazole and the 2-(thiocyanomethylthio)-benzothiazole in a weight ration of between 5:1 and 2:1 with especially preferred compositions containing the active components in a weight ratio of about 3:1.

The fungistatic compositions preferably contain between about 10 and 70% (preferably about 20–35%, e.g., 33%) of the said substituted benzimidazoles and between about 1 and 20% (preferably about 5–10%) of the 2-(thiocyanomethylthio)-benzothiazole.

The 1-(butylcarbamoyl)-2-benzimidazole carbamic acid methyl ester is the preferred species of the said substituted benzimidazoles as the active component in the fungistatic compositions of this invention.

In addition to the two said active components, the fungistatic compositions may contain the usual range of other adjuvants such as inert carriers, wetting agents, binding agents, etc. These adjuvants are those conventionally used in fungistatic compositions, e.g., those used with the active components, i.e., the substituted benzimidazole and the benzothiazole, separately. If desired, other fungicidal agents may also be incorporated in the fungistatic compositions of the present invention. They may also contain other organic materials which may be associated by-products and/or components of the reaction mixture utilized in the production of the active components.

The fungistatic compositions preferably contain an inert carrier. Although the composition may be liquid, for commercial convenience it is preferably solid and in the form of very fine powders which may, if desired, be granulated. The preferred fungistatic compositions contain a particular solid inert carrier, e.g., bentonite, talc, clay, silica.

The fungistatic compositions of the present invention may be applied to control (and often to substantially completely prevent) fungus attack against the substrate in the same manner as other non-fungistatic compositions. When utilizing liquid compositions, seeds may be sprayed by or even soaked in the liquid compositions. When utilizing the preferred fungistatic compositions, the seeds are physically contacted with the fungistatic composition, for example, by intimately admixing the seeds with the powdered composition and maintain the admixture for a considerable time period as illustrated in the Examples. The amount of fungistatic composition utilized in treating the seed and the length of physical contact before the seed is planted is dependent upon the amount of active component in the fungistatic composition utilized, and upon the service conditions contemplated. This is readily determined by those skilled in this art.

The effectiveness of the synergism of the proposed combination of 1-(butylcarbamoyl)-2-benzimidazole carbamic acid methyl ester and 2-(thiocyanomethylthio)-benzothiazole is demonstrated by the following Examples.

100 g samples of summer barley of the variety "Breuns Wisa" infected with *Helminthosporium sativum Cochliobolus sativus*), brown spot and foot disease of barley, were steeped for about 5 minutes in glass bottles in the following fungicides:

Composition 1

50 mg of the commercial product BENLATE, made by DU PONT, Wilmington, Del., USA. BENLATE, a solid, contains as the active agent 50% of 1-(butylcarbamoyl)-2-benzimidazole carbamic acid methyl ester.

Composition 2

50 mg of the commercial product BUSAN 15, made by BUCKMAN LABORATORIES, INC., Memphis, Tenn., USA. BUSAN 15, a very viscous liquid, contains as the active agent 15% of 2-(thiocyanomethylthio)-benzothiazole.

Composition 3

A mixture of 50 mg of BENLATE and 50 mg of BUSAN 15. This mixture contained 24.5% of 1-(butylcambamoyl)-2-benzimidazole carbamic acid methyl ester, 7.6% of 2-(thiocyanomethylthio)-benzothiazole. 24% of organic material (probably by-products), 10% silicic acid, 20% clay (Ataclay), 10% talc, 0.5% stearic acid, and 1% wetting agent.

Immediately after this treatment (Test 1), as well as 1 week later (Test 2), and 2 weeks later (Test 3), 10 seeds of barley were placed germ-free with a pincette in each of five Petri dishes containing a 2% malt extract agar. For the purpose of control 5 dishes were each provided with 10 seeds of a grain which had not been treated. After having been kept at room temperature in the dark the grains around which the first mouse-grey, subsequently deep black spore-forming fungal lawns of *Helminthosporium sativum* had developed were counted under a binocular. Binocular and occasionally microscopic control are necessary because an Alternaria infection looks very much the same to the naked eye. Moreover, all seeds were counted as being infected that had fungal spores attached to them although no development of mycelium could be detected.

On a 2% malt agar *Helminthosporium sativum* forms large colonies of spores, whereas the two other Helminthosporium species, viz. *Helminthosporium gramineum* and *Helminthosporium teres*, which are responsible for the stripe and net spot disease do not grow on the seed.

The results of these tests are collated in the following Table. The efficiency was calculated by Abbott's formula, viz:

$$\text{Efficiency } \% = \frac{\text{Controls infected} - \text{samples infected}}{\text{controls infected}} \times 100$$

RESULTS after 7 DAYS

| Test | Untreated | Composition 1 BENLATE 50g/ 100 kg Seed | | Composition 2 BUSAN 15 50g/ 100 kg Seed | | Composition 3 BENLATE 50g/ 100 kg Seed + BUSAN 15 50g/ 100 kg Seed | |
|---|---|---|---|---|---|---|---|
| | Infected % | Infected % | Efficiency % | Infected % | Efficiency % | Infected % | Efficiency % |
| 1 | 24 | 22 | 8 | 20 | 17 | 14 | 42 |
| 2 | 30 | 40 | 0 | 28 | 7 | 14 | 53 |
| 3 | 30 | 30 | 0 | 14 | 53 | 10 | 67 |

Test 2 is interesting since only 30% of the untreated controls were infected with *Helminthosporium sativum*, whereas the percentage infection after BENLATE treatment was 40%. This is due to the fact that BENLATE is very effective in the case of the majority of fungi that attack barley (but not in the case of Alternaria and Helminthosporium species) so that the *Helminthosporium sativum* cultures had the field to themselves whereas in the untreated controls everything grows and hence *Helminthosporium sativum is partly suppressed by other more vigorous fungi. The total infection ratio in this case: Cultures in five dishes containing* 50 seeds 15 : 11, in the case of BENLATE 20 : 16, in the case of BUSAN 15 14 : 6, whereas in the case of the mixture it was 7 : 1. This test very clearly shows that an agent for treating seed can be fully successful only if the agent does in fact suppress all the parasitic fungi that can be transmitted by the seed. This general efficacy against all fungi that can attack the seed is therefore a special advantage of the proposed mixture.

It also follows clearly from these tests that the proposed mixture containing the active agents 1-(butylcarbamoyl)-2-benzimidazole carbamic acid methyl ester and 2-(thiocyanomethylthio)-benzothiazole has a synergistic effect on *Helminthosporium sativum*, i.e. that its effect exceeds that of the sum of the effects of like quantities of these substances separately:

| | % efficiency of the mixture | Sum of the efficiencies in % of the individual agents |
|---|---|---|
| Test 1 | 42% | 25% |
| Test 2 | 53% | 7% |
| Test 3 | 67% | 53% |

What is claimed is:

1. A fungistatic composition containing as the active components approximately 3 parts of 1-(butylcarbamoyl)-2-benzimidazole carbamic acid methyl ester and 1 part of 2-(thiocyanomethylthio)-benzothiazole.

2. A method for inhibiting attack of cereal seeds by fungus comprising contacting said cereal seeds with an amount of the fungistatic composition of claim 1 effective to inhibit growth of fungus on said cereal seeds.

3. The method of claim 2, wherein the fungus is a Helminthosporium species.

* * * * *